United States Patent [19]

Romano

[11] Patent Number: 4,850,968
[45] Date of Patent: Jul. 25, 1989

[54] SELF-BLOCKING HYPODERMIC SYRINGE FOR ONCE-ONLY USE, COMPRISING A NEEDLE PROTECTION CAP

[75] Inventor: Armando Romano, Milan, Italy
[73] Assignee: AR.MA.s.r.l., Rome, Italy
[21] Appl. No.: 218,284
[22] Filed: Jul. 13, 1988

[30] Foreign Application Priority Data

Jul. 27, 1987 [IT] Italy .................................. 48229 A/87
Nov. 19, 1987 [IT] Italy .................................. 48624 A/87

[51] Int. Cl.⁴ ................................................ A61M 5/00
[52] U.S. Cl. ...................................... 604/110; 604/218
[58] Field of Search ............... 604/110, 187, 192, 198, 604/263, 218, 220, 88

[56] References Cited

U.S. PATENT DOCUMENTS 4,031,892 6/1977 Hurschman ........................ 604/88 X
4,393,272 7/1983 Staempfli ............................ 604/110

Primary Examiner—John D. Yasko
Attorney, Agent, or Firm—Laurence R. Brown; Alfred J. Mangels

[57] ABSTRACT

The syringe according to the invention comprises elastic means for blocking the intake stroke of the plunger which are initially located in an inactive position and are transferred into an active position during the first syringe intake and injection operation. When in said active position the elastic means are disposed in a position secured to the cylindrical body of the syringe and interfering with the intake stroke of the plunger.

The syringe of the invention also comprises a slidable cap coaxial to the syringe body and covering the body itself, and being provided at its front with an exit hole for the needle and having members for its fastening to the syringe body, and elastic thrust means. The cap when in its retracted position leaves the needle exposed and when in its advanced position covers the needle, the fastening members being moved into their released position by elastic means on the first forward movement of the plunger.

13 Claims, 2 Drawing Sheets

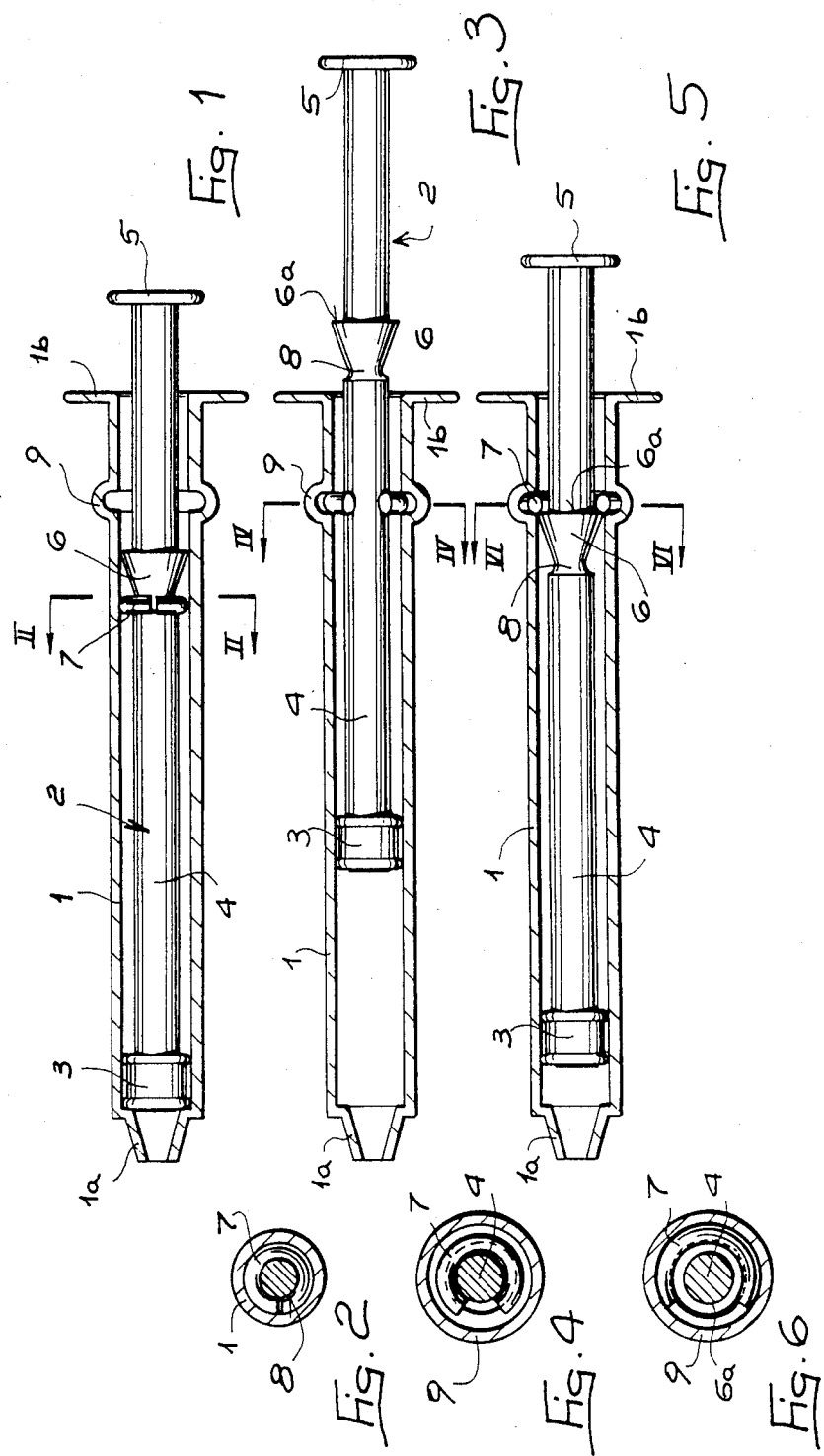

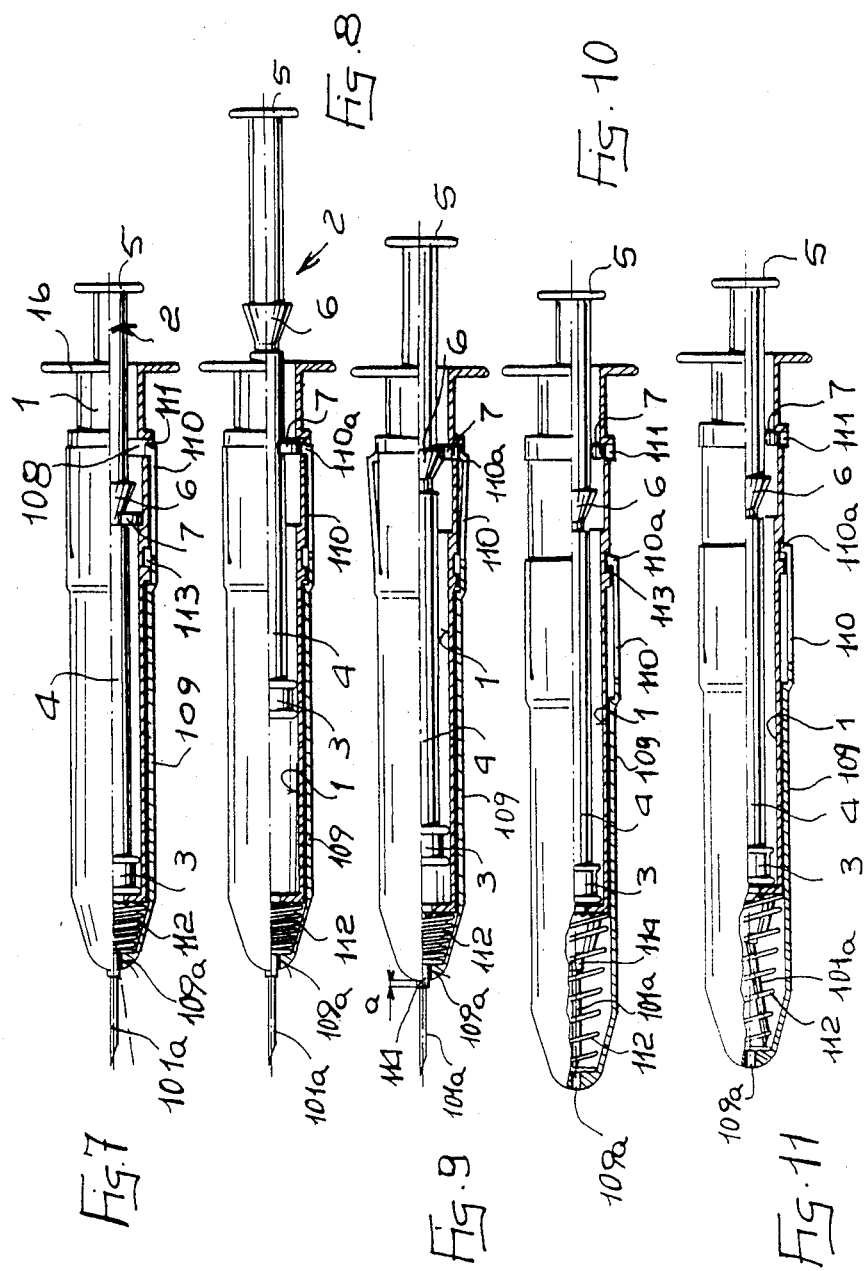

SELF-BLOCKING HYPODERMIC SYRINGE FOR ONCE-ONLY USE, COMPRISING A NEEDLE PROTECTION CAP

BACKGROUND OF THE INVENTION

This invention relates to a self-blocking hypodermic syringe for once-only use, which cannot be reused after it has been once used, and is provided with a needle protection cap which is automatically transferred into its protection position after use.

In medical practice, medicaments are frequently administered to the patient hypodermically by means of a needle and syringe.

In order to ensure maximum protection from infection and the like, sterile syringes for once-only use are usually employed, these being packaged in sealed containers to be opened at the moment of use.

However, syringes are also used by drug addicts for drug injection, and with this category of person a considerable increase has been noted in the spread of viral illnesses, such as type B hepatitis and acquired immunodeficiency syndrome (AIDS), the cause of which is the contagion transmitted by the use of the same syringe by more than one person, who ignore the rule which prescribes its once-only use.

Moreover when syringes are used to inject persons suffering from illnesses of the aforesaid type, it can sometimes happen that the medical functionary or whoever carries out the injection is accidentally injured by the used syringe needle either before fitting a protection cap onto the needle or while fitting it, or before placing the syringe in a closed container for its disposal, with the danger of contracting the infection.

Finally, syringes used by drug addicts for drug taking are very often carelessly thrown away in public places such as public gardens after use, so exposing park attendants and other persons, especially children, to the danger of accidental pricking and possible infection.

Certain syringes comprise means for controlling the plunger stroke within the cylindrical body for various reasons.

For example, GB-A-551 545 discloses a syringe comprising means for delaying or braking the plunger stroke within the cylindrical body and for enabling the user to determine the quantity of injected liquid by feel.

DE-A-3 107 414 discloses blocking means for preventing the extraction of a plunger from the cylindrical body in order to avoid contaminating the space which is to contain the liquid to be injected, and US-A-1 434 381 discloses a syringe provided with elastic braking or delay means to prevent accidental introduction of air into the liquid contained in the syringe or accidental leakage of this liquid, or again accidental escape of the plunger from the cylindrical body.

However, none of the known syringes comprises means for preventing the re-use of a once-only usable syringe or for preventing accidental pricking after the syringe has been used.

The problem therefore arises of preventing the spread of contagion by making it impossible to use the same syringe more than once, independently of the desire or negligence of the user, and of isolating the needle after the syringe has been used so that the needle is made safe.

SUMMARY OF THE INVENTION

These results are attained according to the present invention by a self-blocking hypodermic syringe for once-only use comprising a cylindrical body which at its front end carries means for connection to a hypodermic needle and is open at its opposite end and contains a plunger which slides in a fluid-tight manner and is provided with a gripping rod, characterised by also comprising elastic means for blocking the plunger intake stroke which are initially located in an inactive position and are transferred into an active position during the first syringe intake and injection operation, when in said active position the elastic means being disposed in a position secured to the cylindrical body of the syringe and interfering with the plunger intake stroke.

According to a currently preferred embodiment, the means for blocking the plunger intake stroke consist of a split-ring which before the syringe is initially used embraces the minor diameter region of a frusto-conical portion of the rod, which converges in the direction in which the plunger is driven for injection. The minor diameter region of said frusto-conical portion has a diameter less than the rod diameter and the major diameter region has a diameter substantially equal to or slightly less than the inner diameter of the cylindrical body. The syringe cylindrical body comprises an annular bulge which is able to receive the split-ring when this is drawn in front of it during the initial liquid intake stage, said bulge having an inner diameter greater than the diameter of the major diameter region of the frusto-conical portion plus the thickness of the split-ring and being positioned at a distance from that end of the cylindrical body carrying the needle which exceeds the distance between the front end of the plunger and the rear surface of its frusto-conical portion. When in its undeformed state, the split-ring has an inner diameter less than the maximum diameter of the frusto-conical portion and an outer diameter greater than the inner diameter of the cylindrical body, and is elastically deformable to widen-out into the bulge under the action of the frusto-conical surface as the plunger is driven in.

Before the syringe is initially used, the split-ring is in a position forward of the bulge in the cylindrical body, and is in its elastically deformed contracted state.

The distance between the split-ring when in its initial position, i.e. embracing the minor diameter region of the frusto-conical portion, and the bulge in the cylindrical body is less than the stroke of the plunger which corresponds to the minimum scheduled liquid dosage for which the syringe can be used.

According to a further characteristic, the syringe of the invention also comprises a slidable cap coaxial to the syringe body and covering the body itself, and being provided at its front with an exit hole for the needle and further having members for its fastening to the syringe body, and elastic thrust means, said cap when in its retracted position leaving the needle exposed and when in its advanced position covering the needle, the fastening members being moved into their release position by release means associated with the first forward movement of the plunger.

Specifically, the cap fastening members consist of elastic tongues provided in the rear part of the cap and having their ends turned inwards to form a hook so that when the cap is in its retracted position they become inserted into corresponding slots in the syringe body to axially lock the cap, the release means consisting of an elastic element which is provided within the syringe in a position corresponding to the slots in the syringe body which house the hook-shaped ends of the cap tongues and is arranged to be radially deformed by the forward stroke of the plunger during the first injection, so urging the hook-shaped ends out of the relative slots.

The syringe body also possesses one or more recesses for receiving the cap tongue fastening elements when the cap is in its advanced position in which it encloses the needle, to thus blocking any further sliding of the cap and prevent its escape.

The elastic element inside the syringe, which urges the hook-shaped ends out of the relative slots, consists of the split-ring which before the syringe is used embraces the minor diameter region of the forwarding converging frusto-conical portion of the plunger, and is arranged to be dragged during the intake stroke into an inner annular cavity in the cylindrical syringe body into which the body slots housing the hook-shaped ends of the tongues open, the split-ring being radially deformable outwards under the action of the frusto-conical portion during plunger advancement.

The elastic means for urging the cap into its advanced position consist of a spiral spring interposed between the front surface of the syringe body and the front end of the plunger, said elastic means being preloaded by the cap being placed in its retracted position, before the syringe is used.

Under the initial conditions, before the syringe is used, the front end of the cap is rearward of the base of the needle by a distance equal to the distance through which the cap has to be advanced in order to completely release the hook-shaped ends of the cap tongues from the respective slots in the syringe body without their re-insertion into the slots being possible.

The hook-shaped ends of the cap tongues have their outer surface bevelled towards the rear of the syringe, and in correspondence with these the recesses in the syringe body which receive the cap tongue fastening elements when the cap is in its advanced position have an undercut rear wall to cause the tongues to deflect inwards should the cap receive a rearward thrust.

According to a particular embodiment, the needle can have its axis oblique to the axis along which the cap slides on the syringe body, and is elastically flexible during the sliding of the cap, after completion of this sliding it returning to its initial oblique axis position within the cap with its free front end laterally displaced from the axis of the front hole in the cap.

The cap is preferably constructed of transparent material, to allow the quantity of liquid present in the syringe body to be seen.

DESCRIPTION OF THE DRAWINGS

The invention will be more apparent from the description of its currently preferred embodiment which is given hereinafter by way of non-limiting example with reference to the accompanying drawings, in which:

FIG. 1 is an axial section through the syringe according to the invention ready for drawing in liquid, and with its protection cap removed for reasons of clarity;

FIG. 2 is a section on the line II—II of FIG. 1;

FIG. 3 shows the syringe of FIG. 1 during liquid draw-in;

FIG. 4 is a section on the line IV—IV of FIG. 3;

FIG. 5 shows the syringe of FIG. 1 during injection;

FIG. 6 is a section on the line VI—VI of FIG. 5;

FIG. 7 is an axial section through the syringe according to the invention in its initial position ready for drawing in liquid, but with its protection cap fitted;

FIG. 8 shows the syringe of FIG. 7 in an intermediate stage during draw-in;

FIG. 9 shows the syringe of FIG. 7 when nearly at the end of the injection stage;

FIG. 10 shows the syringe of FIG. 7 after use, with the needle protected; and

FIG. 11 shows an alternative embodiment of the syringe of FIG. 7 after use.

DETAILED DESCRIPTION

As shown in FIG. 1, the syringe according to the invention comprises an outer cylindrical body 1 having a front end 1a shaped to connect to a needle, not shown as it can be of known type, and a rear end 1b provided with a gripping flange. Within the cylindrical body 1 there slides a plunger 2 provided with a seal element 3 and a rod 4 terminating with a gripping flare 5.

As best seen in FIG. 3, the rod 4 carries a frusto-conical portion 6 which converges towards the seal element 3 and has its major diameter substantially equal to or slightly less than the inner diameter of the cylindrical body 1, and its minor diameter less than the diameter of the rod 4.

A toroidal split-ring 7 which when in its rest state has an outer diameter greater than the inner diameter of the cylindrical body 1 and an inner diameter equal to the diameter of the rod 4, is located about the minor diameter region 8 of the portion 6 before initial use, and is therefore housed within the cylindrical body 1 in the position shown in FIG. 1, in a deformed contracted state about the minor diameter region 8 of the portion 6, as can be also seen in FIG. 2.

At a short distance from its rear end 1b, the cylindrical body 1 comprises an annular bulge 9 with an inner diameter equal to the maximum diameter of the frusto-conical portion 6 plus the width of the split-ring 7.

Under the initial conditions, as shown in FIGS. 1 and 2, the split-ring 7 is contracted about the minor diameter region 8 of the frusto-conical portion 6, and the plunger 2 is inserted completely into the cylindrical body 1, with the ring 7 in an intermediate position between the end 1a of the cylindrical body 1 and the annular bulge 9.

For its use, the syringe must be filled by drawing the medicinal liquid in by withdrawing the plunger 2 rearward. During this stage, as shown in FIG. 3, the ring 7 is pulled by the rod 4 towards the annular bulge 9, into which it becomes inserted by opening out elastically into its rest state, shown in FIG. 4.

The liquid intake stage can then be continued until the syringe is filled with the required volume of medicinal liquid, without any further movement of the ring 7 which remains securely housed in its seat, whereas the plunger 2 can be moved to expel residual air or the like before inserting the needle into the patient's body for injecting the medicament.

During the subsequent injection stage, the plunger 2 is driven in to expel the liquid contained in the syringe, until the frusto-conical portion 6 comes into contact with the split-ring 7. During advancement of the plunger 2, the action of the surface of the portion 6 causes the ring 7 to widen out into its dilate state shown in FIG. 6, with its inner diameter equal to the maximum diameter of the portion 6, so allowing the portion 6 to pass through as shown in FIG. 5, and enabling the plunger 2 to terminate its stroke in order to completely expel the contained liquid.

When the frusto-conical portion 6 of the plunger 2 has passed beyond the ring 7, this elastically assumes its rest state, held within the bulge 9 and abutting against the flat rear surface 6a of the frusto-conical portion 6 and thus opposing any subsequent withdrawal of the plunger 2. As the flat rear surface 6a of the frusto-conical portion 6 has a diameter substantially equal to or slightly less than the inner diameter of the cylindrical body 1, even if the ring 7 is forced and/or fractured it will be absolutely impossible to withdraw the plunger 2 due to interference.

This configuration therefore makes it no longer possible to draw further liquid in, so making any second utilisation of the syringe impossible.

The distance between the syringe front end 1a and the bulge 9 and the distance between the front surface of the seal element 3 and the surface 6a are such that the position to which the plunger 2 has advanced when the ring 7 abuts against the surface 6a is such as not to allow sufficient liquid to be injected before this abutment occurs, and also such as to allow the ring 7 to be drawn into the bulge 9 during the intake stage with even the minimum usable dosage of medicinal liquid, so as to prevent situations occurring in which the plunger does not become blocked after the initial injection, either by accident or by purposeful manipulation.

With reference to FIG. 7, the syringe according to the invention is also provided with a cap 109 which is of transparent material to enable the quantity of liquid present in the syringe to be seen, and has at its front a hole 109a for passage of the needle 101a, the cap being provided in its rear part with at least two elastic tongues 110 having their free ends 110a turned inwards in the manner of a hook and inserted, when under initial conditions, in respective slots 111 which open into the groove 108.

Between the body 1 and the front end of the cap 109 there is also provided a spring 112, for example of spiral type, which under initial conditions is compressed. The body 1 is also provided with an outer annular cavity 113 or several limited cavities, disposed in correspondence with the free ends 110a of the tongues 110.

For its use, the syringe must be filled by drawing the medicinal liquid in by withdrawing the plunger 2 rearward. During this stage, as shown in FIG. 8, the ring 7 is pulled by the rod 4 towards the annular groove 108, into which it becomes inserted by opening out elastically into its rest state, in contact with the ends 110a of the tongues 110.

The liquid intake stage can then be continued until the syringe is filled with the required volume of medicinal liquid, without any further movement of the ring 7 which remains securely housed in its seat, whereas the plunger 2 can be moved to expel residual air or the like before inserting the needle into the patient for injecting the medicament.

During the subsequent injection stage, the plunger 2 is driven in to expel the liquid contained in the syringe, until the frusto-conical portion 6 comes into contact with the split-ring 7. During advancement of the plunger, the action of the surface of the portion 6 causes the ring 7 to widen out to an inner diameter equal to the maximum diameter of the portion 6, so allowing the portion 6 to pass and enabling the plunger 2 to terminate its stroke in order to completely expel the liquid contained in the syringe.

During this stage the ring 7 has widened out to the maximum diameter of the groove 108, and its outer surface therefore acts against the ends 110a of the tongues 110 to urge them outwards, as shown in FIG. 9, so that they deflect until they become released from the engagement with the edge of the groove 108.

Under the action of the spring 112, the cap 109 then advances through a distance "a" equal to the needle terminal portion 114 which determines its maximum depth of insertion, so that it comes into contact with the skin of the patient, against which it remains until the injection is complete, while the ends 110a of the tongues 110 rest against the outer wall of the body 1 in a position forward of the groove 108, so that they are unable to re-enter the relative slots 111.

When the frusto-conical portion 6 of the plunger 2 has passed beyond the ring 7, it elastically assumes its rest state, held within the groove 108 and abutting against the flat rear surface 6a of the frusto-conical portion 6 and thus opposing any subsequent rearward movement of the plunger 2.

This therefore makes it no longer possible to draw further liquid in, so making any second utilisation of the syringe impossible. At the same time, with the extraction of the needle, the cap 109 advances under the thrust of the spring 112 into the configuration shown in FIG. 10, in which it entirely encloses the needle, and the ends 110a of the tongues 110 become inserted into the cavity 113, to prevent any further advancement.

That wall of the cavity 113 located towards the rear of the syringe is undercut, and the rear wall of the end 110a of the tongues 110 is shaped to correspond to this undercut. In this manner, the tongues oppose any force which could tend to again move the cap 109 rearward, so keeping the needle covered and preventing any accidental pricking by the used needle.

As shown in FIG. 11 and by an axis line in FIG. 7, the needle 101a can be formed with its axis inclined to the axis of advancement of the cap 109, or in any event not coinciding with the syringe axis. In this manner, when the cap slides forward the needle undergoes deflection until it is completely housed within the cap, where it then straightens so that its point is displaced sideways from the front hole 109a of the cap 109, thus making any further retraction of the cap 109 and consequent exposure of the needle impossible, even under conditions of accidental or voluntary breakage or bending of the tongues 110.

The dimensions of the syringe according to the invention can be freely chosen according to utilisation requirements, and materials of various types can be used compatible with sterisability and absence of toxicity, and compatible with the medicinal substances injected.

What is claimed is:

1. A self-blocking hypodermic syringe of the type wherein a plunger is withdrawn for an intake stroke of liquid before dispensing the liquid, with the syringe operable for once-only use comprising a cylindrical body which at its front end carries means for connection to a hypodermic needle and is open at its opposite end, a plunger which slides in a fluid-tight manner and is provided with a gripping rod, elastic means for blocking the intake stroke of the plunger which are initially located in an inactive position and are transferred into an active position during the first syringe intake and injection operation, and structure operable when the plunger is placed in said active position by a first intake stroke to dispose the elastic means in a detent position securing the elastic means to the cylindrical body of the syringe and operable to prevent a further plunger intake stroke.

2. A self-blocking hypodermic syringe for once-only use comprising a cylindrical body which at its front end carries means for connection to a hypodermic needle and is open at its opposite end, and contains a plunger which slides in a fluid-tight manner and is provided with a gripping rod, characterized by also comprising elastic means for blocking the intake stroke of the plunger which are initially located in an inactive position and are transferred into an active position during first syringe intake and injection operation, when in said active position the elastic means being disposed in a position secured to the cylindrical body of the syringe and interfering with the plunger intake stroke, said elastic means consisting of a split-ring which before the syringe is initially used embraces the minor diameter region of a frusto-conical portion of the rod of the plunger which converges in the direction in which the plunger is driven for injection, the minor diameter region of the frusto-conical portion having a diameter less than the diameter of the rod and the major diameter region having a diameter substantially equal or slightly less than the inner diameter of the cylindrical body, the syringe cylindrical body comprising an annular bulge which is able to receive the slit-ring when this drawn in front of it during the initial liquid intake stage, said bulge having an inner diameter greater than the diameter of the major diameter region of the frusto-conical portion plus the thickness of the slit-ring and being position at a distance from that end of the cylindrical body carrying the needle which exceeds the distance between the front end of the plunger and the rear surface of its frusto-conical portion, when its undeformed state the split-ring having an inner diameter less than the maximum diameter of the frusto-conical portion and an outer diameter greater than the inner diameter of the cylindrical body, and being elastically formable to widen out into the bulge under the action of the frusto-conical surface as the plunger is driven in.

3. A syringe according to claim 2, characterized in that before the syringe is initially used, the split-ring is in a position forward of the bulge in the cylindrical body, and is in an elastically deformed contracted state.

4. A syringe according to claim 3, characterised in that the distance between the split-ring when in its initial position, i.e. embracing the minor diameter region of the frusto-conical portion, and the bulge in the cylindrical body is less than that stroke of the plunger which corresponds to the minimum scheduled liquid dosage for which the syringe can be used.

5. A self-blocking hypodermic syringe for once-only use comprising a cylindrical body which at its front end carries means for connection to a hypodermic needle and is open at its opposite end, and contains a plunger which slides in a fluid-tight manner and is provided with a gripping rod, characterized by also comprising elastic means for blocking the intake stroke of the plunger which are initially located in an inactive position and are transferred into an active position during the first syringe intake and injection operation, when in said active position the elastic means being disposed in a position secured to the cylindrical body of the syringe and interfering with the plunger intake stroke, said hypodermic syringe being further characterized by comprising a slidable cap coaxial to the syringe body and covering the body itself, and being provided at its front with an exit hole for the needle, and further having members for its fastening to the syringe body, and elastic thrust means, said cap when in its retracted position leaving the needle exposed and when in its advanced position covering the needle, the fastening members being moved into their released position by release means associated with the first forward movement of the plunger.

6. A syringe according to claim 5, characterised in that the cap fastening members consist of elastic tongues provided in the rear part of the cap and having their ends turned inwards to form a hook so that when the cap is in its retracted position they become inserted into corresponding slots in the syringe body to axially lock the cap, the release means consisting of elastic means for blocking the intake stroke of the plunger, which are provided within the syringe in a position corresponding with the slots in the syringe body which house the hook-shaped ends of the tongues provided on the cap, and are arranged to be radially deformed by the forward stroke of the plunger during the first injection, so urging the hook-shaped ends out of the relative slots.

7. A syringe according to claim 6, characterised in that the syringe body also possesses one or more recesses for receiving the fastening elements on the tongues of the cap when the cap is in its advanced position in which it encloses the needle, to thus block any further sliding of the cap and prevent its escape.

8. A syringe according to claim 6, charaterised in that the elastic element inside the syringe, which urges the hook-shaped ends out of the relative slots, consists of the split-ring which before the syringe is used embraces the minor diameter region of a forwardly converging frusto-conical portion of the rod of the plunger, and is arranged to be dragged during the first intake stroke into an inner annular cavity in the cylindrical syringe body into which the slots in the body which house the hook-shaped ends of the tongues open, the split-ring being radially deformable outwards under the action of the frusto-conical portion during forward movement of the plunger.

9. A syringe according to claim 5, characterised in that the elastic means for urging the cap into its advanced position consist of a spiral spring interposed between the front surface of the syringe body and the front end of the plunger, said elastic means being preloaded by the cap being placed in its retracted position, before the syringe is used.

10. A syringe according to claim 5, characterised in that under the initial conditions, before the syringe is used, the front end of the cap is rearward of the base of the needle by a distance equal to the distance through which the cap has to be advanced in order to completely release the hook-shaped ends of the tongues on the cap from the respective slots in the syringe body without their re-insertion into the slots being possible.

11. A syringe according to claim 7, characterised in that the hook-shaped ends of the cap tongues have their outer surface bevelled towards the rear of the syringe, and in correspondence with these the recesses in the syringe body which receive the cap tongue fastening elements when the cap is in its advanced position have an undercut rear wall to cause the tongues to deflect inwards should the cap receive a rearward thrust.

12. A syringe according to claim 5, characterised in that the needle has its axis oblique to the axis along which the cap slides on the syringe body, and is elastically flexible during the sliding of the cap, after completion of this sliding it returning to its initial oblique axis position within the cap with its free front end laterally displaced from the axis of the front hole in the cap.

13. A syringe according to claim 5, characterised in that the cap is constructed of transparent material, to allow the quantity of liquid present in the syringe body to be seen.

* * * * *